United States Patent [19]

Sugano

[11] Patent Number: 5,496,705
[45] Date of Patent: Mar. 5, 1996

[54] MONOCLONAL ANTIBODY SPECIFIC FOR RAT SYNAPTOPHYSIN

[75] Inventor: Mitsuko Sugano, Tokyo, Japan

[73] Assignee: Kabushiki Kaisha Toshiba, Kawasaki, Japan

[21] Appl. No.: 224,195

[22] Filed: Apr. 7, 1994

Related U.S. Application Data

[63] Continuation of Ser. No. 929,377, Aug. 14, 1992.

[30] Foreign Application Priority Data

Aug. 16, 1991 [JP] Japan .................................. 3-229756

[51] Int. Cl.$^6$ ..................... G01N 33/53; G01N 33/574
[52] U.S. Cl. ..................... 435/7.23; 435/7.21; 435/7.1; 435/960; 530/388.2; 530/388.8; 530/388.85; 436/548
[58] Field of Search ............................ 435/7.1, 7.9, 960, 435/7.92–7.95, 7.23, 240.27, 70.21, 7.21; 530/388.2, 388.85, 388.8, 389.7; 436/813, 513, 548

[56] References Cited

U.S. PATENT DOCUMENTS 4,434,227  2/1984  Unger .......................................... 435/5
4,487,829  12/1984  Sharp et al. ................................ 435/5

FOREIGN PATENT DOCUMENTS 0431567  6/1991  European Pat. Off. .
0449269  10/1991  European Pat. Off. .
WO83/04313  12/1983  WIPO .

OTHER PUBLICATIONS

File Server STN Karlsruhe, File Medline, AN-88087379.
Buckley, K. M., et al. J. Cell. Biol., Dec. 1987, vol. 105 (6 PT 1) 2447–56.
Bertram Wiedenmann et al., "Identification And Localization Of Synaptophysin, AN Integral Membrane Glycoprotein Of $M_1$ 38,000 Characteristic Of Presynaptic Vesicles," Cell vol. 41, pp. 1017–1028 (Jul., 1985).
Reinhard Jahn et al, "A 38,000–Dalton Membrane Protein (p. 38) Present In Synaptic Vesicles," Proc. Natl. Acad. Sci. USA, vol. 82, pp. 4137–4141 (Jun., 1985).
Kunihiko Obata et al, "Identification Of A Synaptic Vesicle–Specific 38,000–Dalton Protein By Monoclonal Antibodies," Brain Research, 375, pp. 37–48 (1986).
Baldwin R. W., et al. Monoclonal antibodies for Cancer detection and Therapy, Orlando, Fla.: Academic Press, 1985, p. 20.
Harlow, E, et al. Antibodies: A Laboratory Manual. Cold Spring Harbor, N.Y.: Cold Spring Harbor Laboratory, pp. 321–323.
Wiedenmann B. et al. "Synaptophysin Identified in Metastases of Neuroendocrine Tumors by Immunocytochemistry and Immunoblotting." American Journal of Clinical Pathology 88(5) 560–569, 1987.
Rose, N. R. et al., eds. Methods in Immunodiagnosis. New York: John Wiley & Sons, 1980, pp. 143–146.
Campbell, A. M. Monoclonal Antibody Technology. New York: Elsevier, 1987, pp. 99–100.
Leube et al (1987) Embo J. 6(11):3261–3268.
Südhof et al (1987) Nucl. Acids Res. (15/22):9607.
Buckley et al (1987) J. Cell Biol. 105: 2447–2456.
Roitt, I. M. "Essential Immunology", Blackwell Scientific Publications, London. 1991 (7th Ed.), pp. 130–133.
Goding, J. W. (1983) "Monoclonal Antibodies: Principles and Practice", Academic Press, N.Y., pp. 56–91.
Sugano et al (1990) Zool. Sci. (Tokyo)7(6):1168.
Roitt, I. M. (1991) In "Essential Immunology", Blackwell Scientific Publications, Oxford, pp. 45–49.

*Primary Examiner*—Toni R. Scheiner
*Assistant Examiner*—Lora M. Green
*Attorney, Agent, or Firm*—Oblon, Spivak, McClelland, Maier & Neustadt

[57] ABSTRACT

An object of this invention is to provide a monoclonal antibody which can quantitatively analyze a very small amount of synaptophysin present in tissues using a small amount of the antibody in accordance with a complement fixation test. Disclosed is a monoclonal antibody produced by using a rat brain extract as an immunogen, wherein an immunoglobulin class thereof is IgM, and the monoclonal antibody has specific reactivity for rat synaptophysin or P-38.

8 Claims, 3 Drawing Sheets

```
   1‾    AGCACCTGGCGATGCCTACGGCGATGCGGGCTACGGGCAGGGCCCCGGAGGCTAT
         *******************************************************
 721"  CAACCAGCACCTGGCGATGCCTACGGCGATGCGGGCTACGGGCAGGGCCCCGGAGGCTAT

56‾  GGGCCCCAGGACTCCTACGGGCCTCAGGGTGGTTATCAACCCGATTACGGGCAGCCAGCC
       ******* ****************************************************
 781"  GGGCCCCAAGACTCCTACGGGCCTCAGGGTGGTTATCAACCCGATTACGGGCAGCCAGCC

116‾  AGCGGTGGCGGTGGCTACGGGCCTCAGGGCGACTATGGGCAGCAAGGCTATGGCCAACAG
       ************************************************************
 841"  AGCGGTGGCGGTGGCTACGGGCCTCAGGGCGACTATGGGCAGCAAGGCTATGGCCAACAG

176‾  GGTGCGCCCACCTCCTTCTCCAATCAGATGTAATCTGGTCAGTGAAGTCCATGAAGATCC
       *************************************************  **********
 901"  GGTGCGCCCACCTCCTTCTCCAATCAGATGTAATCTGGTCAGTGAAGTTCATGAAGATCC

236‾  CACGGGTGGGCAAGAGCTCAAGAGAAGGCCTGCCCCCCTTTTCCCATCCCCATATCCTAG
       ************************************************************
 961"  CACGGGTGGGCAAGAGCTCAAGAGAAGGCCTGCCCCCCTTTTCCCATCCCCATATCCTAG

296‾  GTCTCCACCCCTCAACCCAGGAGACCCTAACTGTCTTTGCTGTTTATATATATATATATT
       * **********************************************************
1021"  GCCTCCACCCCTCAACCCAGGAGACCCTAACTGTCTTTGCTGTTTATATATATATATATT

356‾  ATATATAAATATCTATTTATCTGTCTGAGCCCTACATTCACCCACTTCTCCATGCACTAG
       ************************************************************
1081"  ATATATAAATATCTATTTATCTGTCTGAGCCCTACATTCACCCACTTCTCCATGCACTAG
```

FIG. 2A

```
 416´ AGGCCCAGTCCTGAATGGGCTCCTCCCCAACCCTGACCTTGCATTCCTCAGCCCCTATCT
      ************************************************************
1141´´ AGGCCCAGTCCTGAATGGGCTCCTCCCCAACCCTGACCTTGCATTCCTCAGCCCCTATCT

476´ GTTCCCCAGCCCTGTCCCTTGAGGTAAGGGGCTCTAGAAAGGGGACAGGAAGGGAACCAG
      ************************************************************
1201´´ GTTCCCCAGCCCTGTCCCTTGAGGTAAGGGGCTCTAGAAAGGGGACAGGAAGGGAACCAG

536´ ACCTTGGCTGCATGGAGTGGGTTGGTGTGACTTTCTCTCCTTCCTCCTCTCCCTCTGCCC
      ************************************************************
1261´´ ACCTTGGCTGCATGGAGTGGGTTGGTGTGACTTTCTCTCCTTCCTCCTCTCCCTCTGCCC

596´ CTCCTAACTCTGGCCTTGGTCCTCCAGCATCACCTGAACTTCAGAAGCTCTCGAATGGAA
      ************************************************************
1321´´ CTCCTAACTCTGGCCTTGGTCCTCCAGCATCACCTGAACTTCAGAAGCTCTCGAATGGAA

656´ ATCTGACCCCAAGAGTAGAGCAGTAGACTGAGTGGAGGAGGCTTGGGTGAAACGGGCAGA
      ************************************************************
1381´´ ATCTGACCCCAAGAGTAGAGCAGTAGACTGAGTGGAGGAGGCTTGGGTGAAACGGGCAGA

716´ GAGGAGATAACCTCTGTAGAGAGAGGACTAGTCAG
      ***********************************
1441´´ GAGGAGATAACCTCTGTAGAGAGAGGACTAGTCAGCCAAGAGTTGAATTCCAGACATACT
```

F I G. 2B

MONOCLONAL ANTIBODY SPECIFIC FOR RAT SYNAPTOPHYSIN

This is a continuation of application Ser. No. 07/929,377, filed Aug. 14, 1992, abandoned.

BACKGROUND OF THE INVENTION

1. Field of the Invention

The present invention relates to a monoclonal antibody which specifically recognizes a synaptophysin.

2. Description of the Related Art

A synaptophysin was found in a bovine brain by wiedenmann et al. in 1985 (Cell, 41, 1017–1028), the synaptophysin being an acidic glycoprotein which is present on the membrane of a synaptic vesicle and has a molecular weight of about 38,000. On the other hand, a P-38 was found in a rat brain by Jahn et al. in 1985 (Proc. Natl. Acad. Sci. USA, 82, 4137–4141). However, when nucleotide sequences of the synaptophysin and the P-38 were analyzed, they were found to be identical proteins.

Since the synaptophysin and the P-38 locally exist in synaptic vesicles, they are used as detection markers for a neuroendocrine tumor which holds synaptic vesicles. The neuroendocrine tumor is formed in endocrine organs having synaptic vesicles such as a pituitary gland and a pancreas, but the tumor is metastasized to a organ other than the endcrine organ, which has no synaptic organs. If the synaptophysin is detected in an organ having no synaptic vesicles, it is understood that the organ holds the tumor and that the tumor is metastasized from the endcrine organ mentioned above. Thus, the synaptophysin specific monoclonal antibody of the present invention is useful to locate a primary focus of the neuroendocrine tumor.

At present, commercially available monoclonal antibody for the synaptophysin or the P-38 is monoclonal antibody which belongs to an immunoglobulin class G.

Since the conventional known monoclonal antibody for the synaptophysin belongs to an immunoglobulin class G, only two binding sites for antigen and complement are present within each molecule. For this reason, in order to quantitatively analyze a very small amount of synaptophysin in tissues in accordance with a complement fixation test, a large amount of the antibody is required, resulting in inconvenience.

SUMMARY OF THE INVENTION

The present invention has been made in consideration of the above situation, and the object of the invention is to make it possible to perform the quantitative analysis of the synaptophysin in accordance with a complement fixation test, by using a small amount of the antibody, even if the amount of the synaptophysin in a biological tissue is very small. More specifically, the object of the present invention is to provide a synaptophysin specific monoclonal antibody belonging to an immunoglobulin class of M.

According to the present invention, there is provided a monoclonal antibody produced by using an extract of a rat brain as an immunogen, the monoclonal antibody belonging to an immunoglobulin class M, and the monoclonal antibody having specific reactivity for a synaptophysin or P-38.

According to the present invention, there is also provided a monoclonal antibody having specific reactivity for a protein expressed from a gene comprising the nucleotide sequence represented by sequence No. 1 in a sequence listing.

(wherein A, C, G, and T represent adenine, cytosine, guanine, and thymine, respectively).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

FIGS. 2A to 2B are views showing a homology between the nucleotide sequence of a rat synaptophysin gene obtained and ascertained by the present invention and the nucleotide sequence of a known rat synaptophysin gene.

DETAILED DESCRIPTION OF THE PREFERRED EMBODIMENTS

Figure 1:
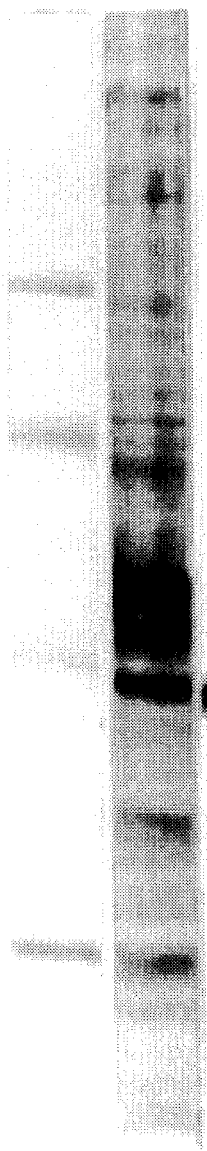
FIG. 1 is a photograph showing the SDS-PAGE development pattern of a rat brain homogenate and specificity of a monoclonal antibody of the present invention.

The present invention will be described in detail below.

Preparation of a monoclonal antibody according to the present invention is explained first.

The monoclonal antibody can be prepared in accordance with a conventional monoclonal antibody technique. That is, an antibody producing cell collected from a mammalian animal immunized with a rat brain extract is fused with an appropriate tumor cell (e.g. a myeloma) of an animal, to prepare a hybridoma producing an objective antibody. This hybridoma is cloned and cultured to obtain a monoclonal antibody according to the present invention.

More specifically, a monoclonal antibody according to the present invention can be prepared in accordance with the following procedures.

a) Preparation of Antibody Producing Cell

In order to obtain a hybridoma producing a monoclonal antibody according to the present invention, a mammalian animal is immunized using a rat brain extract.

As the mammalian animal for obtaining a cell producing a monoclonal antibody according to the present invention, a general laboratory animal such as a mouse, a rat, a rabbit, and a guinea pig can be used, but the mouse is preferably used.

As a method of immunizing a mammalian animal, a method of injecting a rat brain extract as an immunogen into, e.g., a mouse intraperitoneally or subcutaneously, can be used. A dosage per injection is preferably 0.2 ml/mouse of the immunogen, which is used for injection as a mixture with an equivalent amount of an adjuvant. This injection is repeated every one or two weeks and performed several times. Final immunization is performed by injecting 0.2 to 0.4 ml/mouse of the immunogen intravenously or intraperitoneally without mixing it with the adjuvant. A spleen of the mouse is excised 3 to 4 days after the final immunization injection, thereby obtaining an antibody producing cell.

b) Preparation of Tumor Cell

A tumor cell to be fused with the antibody producing cell is prepared as follows.

As a tumor cell according to the present invention, a myeloma cell is generally used. The origin of the tumor cell is not limited to a specific one. Any cell line derived from a mammalian animal such as a mouse, a rat, a rabbit, or human can be used. Among them all, a mouse cell line is preferably used. A tumor cell line having an suitable selection marker such as hypoxanthine guanine phosphoribosyl transferase deficiency (HGPRT⁻) or thymidine kinase deficiency (TK⁻) is generally used. Examples of this cell line are P3-X63-Ag8, P3-X63-Ag8-Ul, and SP20-Ag8-6.5.3. All these tumor cells are 8-azaguanine-resistant cell lines and cannot be grown in an HAT medium (containing hypoxanthine, aminopterin, and thymidine).

c) Cell Fusion

The antibody producing cell is fused with the tumor cell.

As a medium used in cell fusion, a medium obtained by adding 10% CS (calf serum), 5% FCS (fetal calf serum)+ 5% CS, or 10% FCS to a generally used essential medium such as an Eagle's minimum essential medium (MEM), a Dulbecco's modified Eagle MEM, or Rosewell Park Memorial Institute (RPMI) 1640 can be used. Any combination of the serum and the essential medium mentioned above can be used for subculturing parent cells. However, when a hybridoma is to be prepared, a medium containing 10% FCS is preferable.

The cell fusion is performed by mixing the two parent cells, that is, the tumor cells (e.g., myeloma) and the immunized splenocytes (i.e., antibody producing cells) at a ratio of 1:5 to 1:20 in the presence of a fusion accelerator. Examples of the fusion accelerator is an HVJ (Hennagglutinating Virus of Japan) and polyethylene glycol (PEG). 30%–50% PEG 1500 is most preferable as the fusion accelerator.

d) HAT Selection of Hybridoma

A hybridoma is selected in the HAT medium. The fused cells obtained by procedure c) are appropriately diluted with e.g., RPMI1640 containing 20% FCS and are seeded in a microculture plate (normally a 96- or 24-well plate) at about $10^4$ to $10^6/100$ µl/well. The HAT selection medium is then added to each well, and the culture is performed while the medium is changed with a new one generally every one to two days.

When an 8-azaguanine resistant cell line is used as tumor cells, nonfused myeloma cells and myeloma-myeloma fused cells die in the HAT medium within about seven days. Also splenocytes cannot be grown over two weeks in-vitro, since they are normal cells and have a predetermined life time. Therefore, all cells growing 7 to 10 days after starting the culture are regarded as spleen-myeloma fused cells.

e) Screening of Hybridoma

The hybridomas selected by procedure d) are screened. The clones of hybridomas which secrete an objective antibody are picked up by a known method such as an ELISA (Enzyme-linked immunosorbent assay), or a immunoblotting method using a culture supernatant of each well in which hybridomas are grown.

f) Cloning

An objective hybridoma obtained by the screening is cloned. Two or more types of hybridomas which produce different antibodies may be grown in each well. For this reason, cloning may be performed using a limiting dilution analysis to obtain single hybridoma clones which produce the objective monoclonal antibody.

g) Acquisition of Monoclonal Antibody

The hybridoma obtained in procedure f) is cultured to obtain the objective monoclonal antibody.

This hybridoma can be cultured in vitro or in vivo. when it is cultured in-vitro, a medium used in this culture can be the above-mentioned medium obtained by adding CS or FCS to the normal medium. After the hybridoma is cultured in this medium for three to five days, the objective antibody can be acquired from the supernatant of the medium. When it is cultured in-vivo, a mineral oil such as pristane(2,6,10, 14-tetramethylpentadecane) is intraperitoneally injected into an animal whose species is same as the origin of the myeloma. After a lapse of at least one week, the hybridoma is intraperitoneally injected. After 7 to 14 days, the abdominal dropsy stayed is sampled to obtain the objective antibody.

Now a gene which expresses synaptophysin recognized by the monoclonal antibody according to the present invention will be described below.

The gene can be obtained by the following procedures. That is, cDNA library prepared from a rat brain using a λgtll vector is transfected into appropriate host cells, thereby expressing the synaptophysin gene. A protein produced by the host cells is screened using an antibody which specifically binds to the rat synaptophysin, thereby selecting a vector in which an objective cDNA fragment is inserted. The selected vector is amplified to obtain the synaptophysin gene.

More specifically, the gene which expresses the synaptophysin recognized by the monoclonal antibody according to the present invention can be prepared by the following procedures.

h) Screening

Host cells (e.g., E.coli) are cultured in an appropriate medium, and a rat brain cDNA library which has been inserted in the λgtll vector available from Clontech Inc. is transfected in the host cells. The cDNA library may be transfected in such a way that, for example, the E.coli is cultured in an appropriate medium such as LBM medium, and then the E.coli suspension is infected with the cDNA-inserted phage vector suspension in the ratio of $5 \times 10^4$ pfu of the phage vector suspension to 1 µl of the E.coli suspension. The resultant mixture is spread on an agar plate and cultured thereon to form plaques. An IPIG soaked N.C. (membrane filter) is placed on the formed plaques, and then incubated. A produced protein by the expression of the cDNA inserted in the vector is transferred to the nitrocellulose membrane.

The anti-synaptophysin monoclonal antibody is reacted with the protein on the nitrocellulose membrane, and then a labeled antibody capable of specifically binding to this anti-synaptophysin antibody is reacted. After the reaction, a treatment required for detecting the marker of the antibody is performed, thereby detecting a spot in which the marker is present. By searching the plaque corresponding to this spot, a vector containing an objective gene fragment for rat synaptophysin can be obtained.

i) Amplification of Vector Containing Rat Synaptophysin Gene

The synaptophysin gene screened by procedure h) is amplified.

The vector confirmed to contain a rat synaptophysin gene fragment can be amplified by culturing the host cell transfected with the vector in accordance with a plate lysate (stock) method or a liquid culture method.

j) Preparation of Rat Synaptophysin Gene

A target gene is prepared from the amplified vector.

Only a phage containing a rat synaptophysin gene fragment is recovered from the host cells. The recovered phage is lysed using chloroform and then proteins are removed with e.g., phenol. After proteins are removed, a DNA containing a rat synaptophysin gene fragment is obtained by precipitating with ethanol.

As described previously, the monoclonal antibody of the present invention can be specifically bound to synaptophysin. Thus, a pharmaceutical composition containing the monoclonal antibody of the present invention and a pharmaceutically acceptable carrier or diluent is useful for the diagnosis of a neuroendocrine tumor which utilizes the presence of synaptophysin as a marker.

For making the diagnosis possible, it is necessary for the monoclonal antibody of the present invention to be labeled. Any marker can be used as far as the marker can be detected after incorporation into a body. However, a radioisotope can be desirably used as a marker because an imaging diagnosis utilizing a scintigraphy method, which is described later, is most popular nowadays. Any radioisotope can be used as a marker depending on the half-life period, kind of radiation, object of diagnosis, etc., though it is desirable to use a radioisotope which is likely to be stored in the desired internal organ. Specific examples of the radioisotopes used as markers include, for example, $^{99m}TC$, $^{111}In$, $^{123}I$, $^{131}I$, $^{201}Tl$, $^{75}Se$, $^{169}Yb$ and $^{67}Ga$.

Any kind of carrier or diluent, which is pharmaceutically acceptable and, thus, used in general, can be used for preparation of the pharmaceutical composition of the present invention. It is also possible to use a plurality of carriers or diluents in combination. It is desirable to use a sterile and aqueous isotonic suspension or solution including, for example, a physiological saline and a phosphate buffer physiological saline.

The pharmaceutical composition of the present invention can be administered by non-oral administration such as subcutaneous administration, intramuscular administration, intravenous administration, or intraperitoneal administration.

The pharmaceutical composition of the present invention can be administered in an amount of 1 to 100 mg/kg, desirably 1 to 10 mg/kg, of a mammal weight, though the amount of administration depends on the age and weight of a patient, method of administration, etc.

The pharmaceutical composition of the present invention can be prepared by a standard method.

Let us describe briefly the diagnostic method using the pharmaceutical composition of the present invention.

A scintigraphy method is most generally employed nowadays for the diagnosis. In the scintigraphy method, an isotope generating a γ-ray is administered into a body. A predetermined period of time later, the distribution of radioactivity of a desired organ or entire body is measured by a scinti scanner or a scinti camera, and the radioactivity distribution thus measured is displayed on a screen as an picture image by fully utilizing an electronic computer. Of course, the displayed picture image is used for the diagnosis for detecting a diseased portion of an organ, i.e., high or low isotope concentration region.

Specifically, a predetermined time after administration of an effective amount of the pharmaceutical composition, a picture image of an organ having a diseased portion (an organ which originally does not have synaptic vesicles), is depicted on a screen, making it possible to perform diagnosis to determine whether the diseased portion is an neuroendocrine tumor or not.

When the monoclonal antibody according to the present invention is used, only synaptophysin among proteins which are transferred to e.g., nitrocellulose, adsorbed in an ELISA plate, or contained in a tissue preparation such as a tissue slice can be easily detected. As its assay method, an indirect enzyme immunoassay or indirect fluorescent antibody technique used in combination with an anti-mouse IgM antibody labeled with an enzyme or a fluorescent dye is exemplified.

The monoclonal antibody according to the present invention belongs to an immunoglobulin class M and has 10 binding sites for antigen or complement within one molecule. When a complement fixation test using the monoclonal antibody according to the present invention is performed, a higher sensitivity can be obtained and a very small amount of rat synaptophysin can be quantitatively analyzed by a smaller amount of the antibody as compared with the analysis using a monoclonal antibody of the conventional IgG class.

It is also possible to perform diagnosis to determine whether the neuroendocrine tumor is metastatic or not by using a pharmaceutical composition containing the monoclonal antibody of the present invention. Further, in the case of using the pharmaceutical composition of the present invention, a diseased portion can be detected more easily by utilizing a scinti scanning method and an electronic computer than in the case of conventional diagnosis using X-rays.

Examples of the present invention will be described in detail below.

EXAMPLE 1

Preparation of Monoclonal Antibody for Proteins of Rat Brain (1) Preparation of Immunogen The following preparation operations were performed at 0° to 4° C., unless otherwise specified. A 0.5 mM protease inhibitor PMSF was added to water and solutions, as needed.

3-fold volume of a buffer solution A (0.32 mM sucrose, 20 mM tris-citric acid buffer solution) was added to a rat brain, and the rat brain was homogenized. The homogenate itself may be used as an immunogen. In Example 1, however, after the homogenate was filtered through a nylon mesh (mesh sizes: 133 μm and 77 μm), the filtered homogenate was layered on an equal volume of buffer solution A and was centrifuged at 1,000 g for 10 minutes. After the centrifugation, the supernatant was recovered. This supernatant was centrifuged at 10,000 g for 30 minutes, and the resultant precipitate was collected (the extract obtained as the precipitate is called a P2 fraction hereinafter). The supernatant obtained by the second centrifugation was further centrifuged at 100,000 g for 150 minutes to collect a precipitate (the extract obtained as this precipitate is called a P3 fraction hereinafter). These fractions were used as an immunogen singly or mixed at an appropriate ratio to obtain an immunogen.

(2) Immunization of Animal

The immunogen prepared in operation (1) and a complete Freund adjuvant in equal volumes were charged in 1-ml syringes. The syringes were connected with needles to stir the immunogen and the complete Freund adjuvant until the immunogen was emulsified with the adjuvant. This emulsion was intraperitoneally injected into a mouse to perform immunization. That is, an experiment was conducted as follows. Basically, the second immunization was performed two weeks after the first immunization. Booster was performed two weeks after the second immunization, thereby completing immunization. Cell fusion was performed three days after the booster. If the number of days had to be adjusted, booster was delayed to adjust the number of days. The antibody titer was assayed such that blood was sampled from the tail vein of the mouse two to seven days after the immunization and immunoblotting (to be described later in detail) was performed using its serum.

(3) Cell Fusion

The mouse immunized by operation (2) was sacrificed by dislocating the cervical vertebrae thereof to take out its spleen. The spleen was placed in a 6-cm dish in which 5 ml of RPMI was placed, and an extra fat was removed from it. The spleen was washed in two 6-cm dishes each containing 5 ml of the RPMI. The spleen was rubbed onto a folded 5 cm square stainless net with pincettes to separate cells. The individually separated cells were transferred to a centrifuge tube and were washed with 10 ml of the RPMI twice by the centrifugation. 0.17M $NH_4Cl$ was added to the precipitated cells to hemorize the cells in ice for 5 minutes. 5 ml of RPMI were added to the cells after the hemolysis and the cells were centrifuged at 1,600 rpm for 5 minutes. The precipitated cells were washed with RPMI and was messed up to have a volume of 20 ml, thereby obtaining a splenocyte suspension.

On the other hand, myeloma in a logarithmic growth phase in an amount corresponding to 2 to 4 dishes were collected by a centrifugation at 1,200 rpm for 5 minutes. The collected myeloma were washed twice with serum-free RPMI and were finally suspended in 10 ml of the RPMI to prepare a myeloma suspension. The numbers of cells contained in the splenocyte suspension and the myeloma suspension were counted, and the myeloma suspension was added to the splenocyte suspension such that the ratio of the number of myeloma to the number of splenocytes was set to be 1/5 to 1/20. The resultant mixture was centrifuged for 5 minutes, the supernatant was removed, and the splenocytes and the myeloma were suspended. All of 0.3 ml of 50% polyethylene glycol 1500 (in 75 mM Hepes) were quickly added to the cells and the cell suspension were immediately stirred well. While stirring was continued, the RPMI was added to the suspension. The resultant suspension was centrifuged at 1,000 rpm for 5 minutes. 50 ml of an HAT medium (an RPMI-FCS containing hypoxanthine having a final concentration of $1\times10^{-7}$M, aminopterin having a final concentration of $4\times10^{-4}$M, and thymidine having a final concentration of $16\times10^{-4}$M) were added to the precipitate. The resultant suspension was seeded in two 24-well plates in an amount of 500 µl/well and in about three 96-well plates in an amount of 100 µl/well. After four to five days, the HAT medium was added to the 24-well plates in an amount of about 1 ml/well and to the 96-well plates in an amount of about 100 µl/well. As a result, it was found that hybridomas grew in almost all wells within about a week. The hybridomas were further cultured, and their supernatants were used for screening according to the immunoblotting method.

(4) Selection and Cloning of Hybridoma

The immunogen prepared in operation (1) was diluted such that a total amount of proteins became several tens of mg/ml, and the resultant diluted solution served as an antigen solution. After the SDS-PAGE of the antigen was performed, the proteins were transferred to a nitrocellulose membrane by electrophoresis in accordance with a method proposed by Towbin et al. (1979). The nitrocellulose membrane was blocked using an appropriate blocking agent such as Block Ace (available from Dainippon-Pharmaceutical Co.) for an hour to overnight. The blocked nitrocellulose membrane was incubated together with the culture supernatant as a primary antibody for screening. Thereafter, the nitrocellulose membrane was washed with TBS three times each for 15 minutes. The nitrocellulose membrane was incubated and reacted with a horseradish peroxidase (HRP-)conjugated goat anti-mouse antibody. The reacted nitrocellulose membrane was washed with TBS three times each for 15 minutes. A color-developing solution obtained by adding 1/100-fold volume of 1% $CoCl_2.6H_2O$, 1/100-fold volume of 1% $(NH_4)2Ni(SO_4)_2.6H_2O$, and 1/500-fold volume of and a hydrogen peroxide solution to 100 µg/ml of diaminobenzidine tetrahydrochloride in 50 mM tris-HCl (pH 7.5) was used to detect a product of color-development reaction. After satisfactory coloring was performed, the nitrocellulose membrane was washed with distilled water and was dried. As a result of a search operation mentioned above, wells from which culture supernatants having a high activity were obtained, were selected. The hybridomas of these wells were cloned by the limiting dilution analysis using mouse thymocytes as feeder cells, thereby obtaining one clone. The hybridoma RB2-4 thus obtained is deposited with the Fermentation Research Institute, the Agency of Industrial Science and Technology, located at 1-3, Higashi 1-chome, Tsukuba-shi, Ibaraki-ken, Japan and assigned the deposit number FERM BP-3944. The hybridoma was cultured to obtain a monoclonal antibody. This monoclonal antibody was named RB2-4.

An examination was performed using a Sub Isotyping Kit available from Amersham, Inc. The subclass of this antibody was found to be an IgM.

EXAMPLE 2

Examination of Reaction Specificity of RB2-4

The reaction specificity of RB2-4 was examined by immunoblotting as in Example 1, and the examination result is shown in FIG. 1.

FIG. 1 is a photograph showing the development pattern of the previously described brain homogenate by the SDS-PAGE and the binding position of RB2-4 by immunoblotting. Referring to FIG. 1, reference numeral 1 denotes a stain pattern of a molecular weight marker by a CBB; 2, a stain pattern of a rat brain homogenate by the CBB; and 3, a result of immunoblotting of the rat brain homogenate by using RB2-4. As can be apparent from FIG. 1, RB2-4 is reacted with a band of a single protein having a molecular weight of about 40 kD.

EXAMPLE 3

Isolation of Rat Synaptophysin Gene (1) Screening of Plaque by using Monoclonal Antibody RB2-4

*E.coli* (Y1090 (ΔlacU169proA+Δlon araD139strAsupF [trpC22::Tn10] (pMC9*),mcrA−,mcrB+)) was cultured overnight using an LBM medium (containing 0.2% maltose and 50 mg/l Ampicillin). A cDNA library (available from Clontech Inc.) constructed from a rat brain using a λgtll vector was diluted to about $4\times 10^5$ pfu. This diluted suspension was mixed with 0.6 ml of an *E.coli* suspension obtained by the above culture, and the mixture was incubated at room temperature for 20 minutes. On the other hand, a top agarose (e.g., LBM agarose) was treated in an autoclave and incubated in a molten state at 55° C. The treated top agarose was mixed with the above mixture, and the resultant mixture was stirred quickly. The resultant mixture was spread on a bottom agar (e.g., 0.8% LMB agar) spread on a plate in advance. After the top agarose was solidified, the solid body was incubated at 42° C. for 3.5 hours to form a plaque. A nitrocellulose membrane was placed on the plaque and was incubated at 37° C. for 3.5 hours, thereby expressing the cDNA transfected in the *E.coli*. This nitrocellulose membrane had been immersed in 10 mM IPTG (isopropylthiogalactopyranoside) and was dried in advance. Thereafter, the nitrocellulose membrane was washed with TBS and was used for subsequent screening by an antigen-antibody reaction.

Screening using RB2-4 was performed as follows. The nitrocellulose membrane was blocked using TBS containing 3% gelatin at room temperature for an hour to overnight.

After the blocked nitrocellulose membrane was reacted with the monoclonal antibody (primary antibody) used in screening, the nitrocellulose membrane was washed with TBS three times each for 15 minutes. Subsequently, the nitrocellulose membrane was reacted with a horseradish peroxidase (HRP)-conjugated goat anti-mouse antibody (secondary antibody). The nitrocellulose membrane was then washed with TBS three times each for 15 minutes. A color-developing solution obtained by adding 1/100-fold volume of 1% $CoCl_2.6H_2O$, 1/100-fold volume of 1% $(NH_4)_2Ni(SO_4)_2.6H_2O$, and 1/500-fold volume of hydrogen peroxide solution to 100 μg/ml diaminobenzidine tetrahydrochloride in 50 mM tris-HCl (pH 7.5) was used to detect a product of color-development reaction. After satisfactory coloring was performed, a plaque corresponding to the stained spot was searched to obtain a phage having an objective gene fragment.

(2) Proliferation of Phage Having Rat Synaptophysin Gene and its Complementary Strand The phage having the rat synaptophysin gene and its complementary strand obtained in operation (1) was proliferated in accordance with the following procedures of the plate lysate method. E.coli (Y1088 (ΔlacU169supEsupFhsdR−hsdM+metBtrpRtonA21 [proc::Tn5] (pMC9),mcrA−mcrB+)) was cultured overnight using LBM medium (containing 0.2% maltose and 50 mg/ml Ampicillin). 0.1 ml of SM buffer solution containing $10^5$ to $10^6$ pfu of the phage was added to the E.coli suspension and was incubated at room temperature for 10 minutes. On the other hand, a top agarose (e.g., LBM agarose) was treated in an autoclave and incubated in a molten state at 55° C. The treated top agarose was mixed with the above mixture, and the resultant mixture was stirred quickly. The resultant mixture was spread on a bottom agar (e.g., LMB agar) spread on a plate in advance. After the top agarose was solidified, the solid body was put into a vinyl bag and cultured at 37° C. for 6 to 7 hours. After the E.coli was lysed, 5 ml of SM buffer solution and some drops of chloroform were added to the solid body. The solid body was incubated overnight at 4° C. while it was held horizontally so that SM buffer solution perfectly covered the surface thereof. As a result, a phage suspension in which a phage having the rat synaptophysin gene and its complementary strand was suspended was obtained.

(3) Preparation of Rat Synaptophysin Gene and its Complementary Strand

5 μg/ml of RNaseA and 5 μg/ml of DNaseI were added to the phage suspension obtained in operation (2), which comprises the rat synaptophysin gene and its complementary strand and the resultant suspension was incubated at 37° C. for 30 minutes. An equal volume of polyethylene glycol PEG 6000-2M NaCl solution was mixed with the above suspension and incubated at 0° C. for an hour. The resultant mixture was centrifuged at 4° C., 3,000 rpm for 20 minutes, and the supernatant was perfectly removed. The resultant precipitate was suspended in 0.5 ml of SM buffer solution, and the suspension was transferred to an eppendorf tube and was centrifuged at 8,000 rpm for 2 minutes. The obtained supernatant was transferred to another eppendorf tube. EDTA and SDS were added to this supernatant so that final concentration of EDTA and SDS is 10 mM and 1% respectively, and the mixture was incubated at 65° C. for 15 minutes. Thereafter, phenol extraction, phenol-chloroform extraction, and chloroform extraction were performed once, twice, and once, respectively. In the phenol extraction or phenol-chloroform extraction, phenol saturated with TE (tris-EDTA buffer solution) was used. 50 μl of 3M sodium acetate and 1 ml of ethanol were added to the aqueous layer obtained by these extraction operations, and the mixture was incubated at −80° C. for 15 minutes and was centrifuged at 15,000 rpm for 5 minutes. After the centrifugation, the supernatant was removed, and the resultant residue was washed with cooled 70% ethanol and was dried. The dried product was dissolved in 50 μl of TE to obtain a phage DNA having the rat synaptophysin gene and its complementary strand.

The rat synaptophysin gene and its complementary strand could be taken from the phage DNA by using restriction enzymes (e.g., EcoRI).

In addition, only the rat synaptophysin gene and its complementary strand were obtained from the phage DNA digested by e.g., EcoRI in accordance with the following procedures. The phage DNA digested by the EcoRI was subjected to electrophoresis using a 1% agarose gel having a low melting point in a buffer system containing ethidium-bromide and TAE (EDTA-tris acetic acid buffer solution). After this electrophoresis, a target band of 0.8 kbp was cut out under Uv radiation by a transilluminator and the target band were transferred to an eppendorf tube. A gel containing the target band were melted at 65° C. and were added with distilled water. The resultant mixture was gradually cooled. After phenol extraction and phenol-chloroform extraction were performed twice and once, respectively, DNA was recovered by ethanol precipitation. In these extractions, phenol saturated with TE was used.

When the nucleotide sequence of the DNA was determined by a dideoxy method, it was found that the DNA comprised a nucleotide sequence represented by sequence No. 1 in a sequence listing. Sequence No. 1 represents the nucleotide sequence of the rat synaptophysin gene obtained in the present invention, and its sequence was represented in a direction toward the 5'-terminus. Herein, A, C, G, and T represent adenine, cytosine, guanine, and thymine, respectively.

Sequence No. 2 in the sequence listing represents the nucleotide sequence of the known rat synaptophysin gene. In this sequence listing, the nucleotide sequence was represented from No. 721 to No. 1,501 from the 5'-terminal to the 3'-terminal. The nucleotide sequence represented by sequence No. 1 according to the present invention corresponds to base Nos. 726 to 1,486 of the known synaptophysin gene.

The homology between the nucleotide sequence of the rat synaptophysin gene obtained in the present invention and the nucleotide sequence of the known rat synaptophysin gene is shown in FIGS. 2A to 2B. The upper row represents the nucleotide sequence of the rat synaptophysin gene obtained by the present invention, and the lower row represents the nucleotide sequence of the known rat synaptophysin gene. An asterisk * indicates an identical base between these base sequences. A, C, G, and T represent adenine, cytosine, guanine, and thymine, respectively; and a mark— represents a position where a nucleotide was deleted. When the gene of the present invention is compared with the known gene, they are identical except for the following three bases:

| Base (No.) of Sequence No. 1 | Corresponding Base (No.) of Sequence No. 2 |
| --- | --- |
| G (64) | A (789) |
| C (224) | T (949) |

-continued

| Base (No.) of Sequence No. 1 | Corresponding Base (No.) of Sequence No. 2 |
|---|---|
| T (297) | C (1022) |

As is apparent from the above comparison, these two DNA sequences are almost identical to each other. That is, the DNA prepared in the present invention is a rat synaptophysin gene.

As has been described above, according to the present invention, there is provided a monoclonal antibody specifically binding to the rat synaptophysin. By using this monoclonal antibody, only the rat synaptophysin can be easily analyzed from proteins transferred to a nitrocellulose membrane in accordance with an indirect enzyme immunoassay or indirect fluorescent antibody technique.

In addition, since the synaptophysin can serve as a good detection marker for neuroendocrine tumors, it is possible to detect neuroendocrine tumors. Therefore, the monoclonal antibody according to the present invention is expected to be used in diagnosis in the clinical and medical fields.

What is claimed is:

1. A method of detecting a neuroendocrine tumor, comprising:

contacting (a) a labeled monoclonal antibody produced by the hybridoma RB2-4, deposited with the Fermentation Research Institute and assigned the Deposit No. FERM BP-3944, said monoclonal antibody being of the immunoglobulin class M and specifically binding rat synaptophysin, or (b) a labeled monoclonal antibody having the identifying characteristics of the monoclonal antibody produced by said hybridoma, with an organ, a tissue slice or a tissue homogenate which may contain synaptophysin, to bind said labelled monoclonal antibody to synaptophysin; and correlating the presence or concentration of said monoclonal antibody bound to said synaptophysin to an indication of a neuroendocrine tumor.

2. The method of claim 1, wherein said neuroendocrine tumor is metastasized, said organ or tissue has no synaptic vesicles, and detecting said monoclonal antibody bound to said synaptophysin is an indication of said metastasized neuroendocrine tumor.

3. The method of claim 1, wherein said labeled monoclonal antibody is labeled with a radioisotope.

4. The method of claim 1, wherein said labeled monoclonal antibody is labeled with a fluorescent marker.

5. A method of effecting or quantitatively analyzing rat synaptophysin, comprising:

performing an immunoassay by contacting a rat tissue homogenate with (a) a monoclonal antibody produced by the hybridoma RB2-4, deposited with the Fermentation Research Institute and assigned the Deposit No. FERM BP-3944, said monoclonal antibody being of the immunoglobulin class M and specifically binding rat synaptophysin, or (b) a monoclonal antibody having the identifying characteristics of the monoclonal antibody produced by said hybridoma, and detecting said monoclonal antibody specifically bound to said rat tissue homogenate to obtain a result of said immunoassay; and correlating said result of said immunoassay to the presence or quantity of said rat synaptophysin.

6. The method of claim 5, wherein said immunoassay is a complement fixation test.

7. The method of claim 5, wherein said monoclonal antibody is labeled with a radioisotope.

8. The method of claim 5, wherein said monoclonal antibody is labeled with a fluorescent marker.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 750 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Rattus norvegicus ( x i ) SEQUENCE DESCRIPTION: SEQ ID NO:1:

```
AGCACCTGGC   GATGCCTACG   GCGATGCGGG   CTACGGGCAG   GGCCCCGGAG   GCTATGGGCC        60
CCAGGACTCC   TACGGGCCTC   AGGGTGGTTA   TCAACCCGAT   TACGGGCAGC   CAGCCAGCGG       120
TGGCGGTGGC   TACGGGCCTC   AGGGCGACTA   TGGGCAGCAA   GGCTATGGCC   AACAGGGTGC       180
GCCCACCTCC   TTCTCCAATC   AGATGTAATC   TGGTCAGTGA   AGTCCATGAA   GATCCCACGG       240
GTGGGCAAGA   GCTCAAGAGA   AGGCCTGCCC   CCCTTTTCCC   ATCCCCATAT   CCTAGGTCTC       300
CACCCCTCAA   CCCAGGAGAC   CCTAACTGTC   TTTGCTGTTT   ATATATATAT   ATATTATATA       360
TAAATATCTA   TTTATCTGTC   TGAGCCCTAC   ATTCACCCAC   TTCTCCATGC   ACTAGAGGCC       420
CAGTCCTGAA   TGGGCTCCTC   CCCAACCCTG   ACCTTGCATT   CCTCAGCCCC   TATCTGTTCC       480
CCAGCCCTGT   CCCTTGAGGT   AAGGGGCTCT   AGAAAGGGGA   GAGGAAGGGA   ACCAGACCTT       540
GGCTGCATGG   AGTGGGTTGG   TGTGACTTTC   TCTCCTTCCT   CCTCTCCCTC   TGCCCCTCCT       600
AACTCTGGCC   TTGGTCCTCC   AGCATCACCT   GAACTTCAGA   AGCTCTCGAA   TGGAAATCTG       660
ACCCAAGAG    TAGAGCAGTA   GACTGAGTGG   AGGAGGCTTG   GGTGAAACGG   GCAGAGAGGA       720
GATAACCTCT   GTAGAGAGAG   GACTAGTCAG                                            750
```

( 2 ) INFORMATION FOR SEQ ID NO:2:

( i ) SEQUENCE CHARACTERISTICS:
        ( A ) LENGTH: 780 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:

( A ) ORGANISM: rat ( x i ) SEQUENCE DESCRIPTION: SEQ ID NO:2:

| | | | | | | |
|---|---|---|---|---|---|---|
| CAACCAGCAC | CTGGCGATGC | CTACGGCGAT | GCGGGCTACG | GGCAGGGCCC | CGGAGGCTAT | 60 |
| GGGCCCCAGG | ACTCCTACGG | GCCTCAGGGT | GGTTATCAAC | CCGATTACGG | GCAGCCAGCC | 120 |
| AGCGGTGGCG | GTGGCTACGG | GCCTCAGGGC | GACTATGGGC | AGCAAGGCTA | TGGCCAACAG | 180 |
| GGTGCGCCCA | CCTCCTTCTC | CAATCAGATG | TAATCTGGTC | AGTGAAGTCC | ATGAAGATCC | 240 |
| CACGGGTGGG | CAAGAGCTCA | AGAGAAGGCC | TGCCCCCTT | TTCCCATCCC | CATATCCTAG | 300 |
| GTCTCCACCC | CTCAACCCAG | GAGACCCTAA | CTGTCTTTGC | TGTTTATATA | TATATATATT | 360 |
| ATATATAAAT | ATCTATTTAT | CTGTCTGAGC | CCTACATTCA | CCCACTTCTC | CATGCACTAG | 420 |
| AGGCCCAGTC | CTGAATGGGC | TCCTCCCCAA | CCCTGACCTT | GCATTCCTCA | GCCCCTATCT | 480 |
| GTTCCCCAGC | CCTGTCCCTT | GAGGTAAGGG | GCTCTAGAAA | GGGGAGAGGA | AGGGAACCAG | 540 |
| ACCTTGGCTG | CATGGAGTGG | GTTGGTGTGA | CTTTCTCTCC | TTCCTCCTCT | CCCTCTGCCC | 600 |
| CTCCTAACTC | TGGCCTTGGT | CCTCCAGCAT | CACCTGAACT | TCAGAAGCTC | TCGAATGGAA | 660 |
| ATCTGACCCC | AAGAGTAGAG | CAGTAGACTG | AGTGGAGGAG | GCTTGGGTGA | AACGGGCAGA | 720 |
| GAGGAGATAA | CCTCTGTAGA | GAGAGGACTA | GTCAGCCAAG | AGTTGAATTC | CAGACATACT | 780 |